US011311584B2

(12) United States Patent
Tran et al.

(10) Patent No.: US 11,311,584 B2
(45) Date of Patent: Apr. 26, 2022

(54) METHOD OF TREATING ALIMENTARY CANAL CONDITIONS

(71) Applicant: Triton Algae Innovations, San Diego, CA (US)

(72) Inventors: Miller Tran, San Diego, CA (US); John Tzu-Yu Chang, San Diego, CA (US); Jon Hansen, San Diego, CA (US); Michael Mayfield, San Diego, CA (US); Stephen Patrick Mayfield, San Diego, CA (US); Beth Ann Rasala, San Diego, CA (US); Xun Wang, San Diego, CA (US)

(73) Assignee: TRITON ALGAE INNOVATIONS, San Diego, CA (US)

( * ) Notice: Subject to any disclaimer, the term of this patent is extended or adjusted under 35 U.S.C. 154(b) by 82 days.

(21) Appl. No.: 16/609,398

(22) PCT Filed: Apr. 27, 2018

(86) PCT No.: PCT/US2018/029791
§ 371 (c)(1),
(2) Date: Oct. 29, 2019

(87) PCT Pub. No.: WO2018/204186
PCT Pub. Date: Nov. 8, 2018

(65) Prior Publication Data
US 2020/0188458 A1 Jun. 18, 2020

Related U.S. Application Data

(60) Provisional application No. 62/492,244, filed on Apr. 30, 2017.

(51) Int. Cl.
| | |
|---|---|
| *A61K 36/05* | (2006.01) |
| *A23K 10/18* | (2016.01) |
| *A23K 10/30* | (2016.01) |
| *A23L 17/60* | (2016.01) |
| *A23L 33/105* | (2016.01) |
| *A23L 33/135* | (2016.01) |
| *A61P 1/00* | (2006.01) |

(52) U.S. Cl.
CPC .............. *A61K 36/05* (2013.01); *A23K 10/18* (2016.05); *A23K 10/30* (2016.05); *A23L 17/60* (2016.08); *A23L 33/105* (2016.08); *A23L 33/135* (2016.08); *A61P 1/00* (2018.01); *A23V 2002/00* (2013.01)

(58) Field of Classification Search
None
See application file for complete search history.

(56) References Cited

U.S. PATENT DOCUMENTS

2013/0302863 A1    11/2013  Geringer et al.

FOREIGN PATENT DOCUMENTS

| CN | 109561711 A | 4/2019 |
| WO | 2018/038960 A1 | 3/2018 |

OTHER PUBLICATIONS

Avila-Roman, J. et al. Microalgae Derived Oxylipins Decrease Inflammatory Mediators by Regulating the Subcellular Location of NFkB and PPAR-g. Pharmacological Research 128:220-230, 2018. (Year: 2018).*
Fields, F. et al. Effects of the Microalgae Chlamydomonas on Gastrointestinal Health. J of Functional Foods 65:1-10. 2020. (Year: 2020).*
Avila-Roman et al. "Preventative effect of the microalga Chlamydomonas debaryana on the acute phase of experimental colitis in rats" British Journal of Nutrition, 2014, 112:1055-1064.
Chen et al. "Heterotrophic Growth of Chlamydomonas reinhardtii on Acetate in Chemostat Culture" Process Biochemistry, 1996, vol. 33, 6:601-604.
Scaife et al. "Establishing Chlamydomonas reinhardtii as an industrial biotechnology host" The Plant Journal, 2015, 82:532-546.
Scranton et al. "Chlamydomonas as a model for biofuels and bio-products production" The Plant Journal, 2015, 82:523-531.
Xiao et al. "Effects of Chitosan on Intestinal Inflammation on Weaned Pigs Challenged by Enterotoxigenic *Escherichia coli*" Plos One, 2014, vol. 9, 8:e104192.
Zhang et al. "Kinetic models for heterotrophic growth of Chlamydomonas reinhardtii in batch and fed-batch cultures" Process Biochemistry, 1999, 35:385-389.
Chassaing et al. "Dextran Sulfate Sodium (DSS)-Induced Colitis in Mice." Current Protocols in Immunology, 2014, 104:Unit15.25:1-16.
Proschold, Thomas, et al., (2018) "*Chlamydomonas schloesseri* sp. nov. (*Chlamydophyceae, Chlorophyta*) revealed by morphology, autolysin cross experiments, and multiple gene analyses", Phytotaza, 362(1):21-38.
Sakurai, Kenta, et al., (2014) "Detection and characterization of phosphatidylcholine in various strains of the genus *Chlamydomonas* (*Volvocales, Chlorophyceae*)", J Plant Res, 127(5):641-50.
Torres, Joana, et al., (2013) "New therapeutic avenues in ulcerative colitis: thinking out of the box", Gut, 62:1642-1652.
Avila-Roman et al. "Preventive Effect of the Microalga Chlamydomonas Debaryana on the Acute Phase of Experimental Colitis in Rats." British Journal of Nutrition, 2014, 112:1055-1064.
Chen et al. "Heterotrophic Growth of Chlamydomonas Reinhardtii on Acetate in Chemostat Culture." Process Biochemistry, Aug. 31, 1996, 31(6):601-604.

(Continued)

*Primary Examiner* — Ralph J Gitomer
(74) *Attorney, Agent, or Firm* — Carol L. Francis; Mandar A. Joshi; Bozicevic, Field & Francis LLP (57) ABSTRACT

Provided herein are methods for the treatment of GI tract diseases and conditions and/or symptoms associated with such diseases and conditions in a mammal. Also provided are preparations and compositions for use in the methods. Also provided are methods of growing and preparing *Chlamydomonas* biomass for administration to a mammal in need of treatment of GI tract diseases and conditions and/or symptoms associated with such diseases and conditions.

19 Claims, 3 Drawing Sheets

(56) References Cited

OTHER PUBLICATIONS

Manuell et al. "Robust Expression of a Bioactive Mammalian Protein in Chlamydomonas Chloroplast." Plant Biotechnology Journal, Mar. 15, 2007, 5(3):402-412.
Avila-Roman et al. "Anti-Inflammatory Effects of an Oxylipin-Containing Lyophilised Biomass from a Microalga in a Murine Recurrent Colitis Model." British Journal of Nutrition, Dec. 27, 2016, 116(12):2044-2052.
PCT/US2018/029791 International Search Report and Written Opinion dated Jul. 24, 2018.

* cited by examiner

METHOD OF TREATING ALIMENTARY CANAL CONDITIONS

CROSS REFERENCE TO RELATED APPLICATION(S)

This application is a US national phase application under 35 U.S.C. § 371 of international patent application no. PCT/US2018/029791, filed Apr. 27, 2018, which claims benefit of priority under 35 U.S.C. § 119(e) of U.S. Ser. No. 62/492,244, filed Apr. 30, 2017, the entire content of each of which is incorporated herein by reference.

BACKGROUND

A number of diseases and conditions involve inflammation or disturbance of the gastrointestinal (GI) tract. Examples include irritable bowel syndrome (IBS), inflammatory bowel disease(s) (BID), Crohn's disease, colitis, ulcerative colitis (UC), and post infection colitis. These conditions can result in persistent and recurrent abdominal pain, irregular bowel movements and symptoms such as diarrhea and in some cases, weight loss. GI tract-related diseases and conditions affect humans and other mammals.

Colitis is a disease of the large intestine or colon in which the lining of the large intestine becomes inflamed. In ulcerative colitis, the intestine develops small sores or ulcers which may produce pus and mucus. The combination of inflammation and ulceration can result in abdominal discomfort and frequent emptying of the bowel.

Colitis is a chronic disease which is characterized by periods of acute symptoms. During the chronic phase, symptoms may lessen or disappear for extended periods of time, but these periods of remission are interrupted by acute episodes of the disease. During acute phases, patients experience persistent bloody diarrhea accompanied by abdominal pain. People suffering from colitis often experience a loss of appetite and have accompanying weight loss. Patients also often experience fatigue and a loss of energy.

In general, colitis is a result of an abnormal function of the immune system. In colitis, the immune system treats the normal contents of the colon as "immunologically foreign" material and mounts an inappropriate inflammatory response. The exact mechanism that causes this inappropriate response is not known, making development of effective treatments more difficult. Genetic make-up may be a factor as colitis tends to run in families, with approximately 20% of patients with colitis also having a relative with the condition. Environmental factors may also play a role as a trigger to start the inappropriate immune response.

Colitis may effect up to 1 million persons in the United States. Men and women are equally likely to be affected with symptoms typically first observed in the mid-thirties, although the condition can occur at any age. Onset of colitis in older people is more often seen in men than in women.

Other examples of GI tract-affecting diseases and conditions include IBS and Crohn's disease. Individuals with IBS often experience persistent and recurrent abdominal pain and symptoms such as diarrhea and/or constipation. IBD is another GI tract condition where the affected individuals may suffer from diarrhea, pain, fatigue, and weight loss. Crohn's disease is generally characterized by symptoms of abdominal pain, diarrhea, vomiting, and weight loss. GI-related symptoms also may be experienced as a result of a microbial infection such as diarrhea caused by enterotoxigenic *E. coli*.

SUMMARY

Provided herein are methods for the treatment of GI tract diseases and conditions in a mammal in need thereof. Such a mammal is one that has been diagnosed as having a GI tract condition or disease such as colitis, irritable bowel syndrome, irritable bowel movement, inflammatory bowel disease (IBD), irritable bowel syndrome (IBS), Crohn's disease, ulcerative colitis, post infection colitis and infection by enterotoxigenic *E. coli*. Provided herein are methods for the treatment of GI tract diseases and conditions in a mammal in need thereof, where the mammal is suffering from one or more symptoms such as diarrhea, abdominal pain, and/or weight loss. In some embodiments, the mammal is diagnosed with or suffers from colitis. In some embodiments, the mammal is diagnosed with or suffers from diarrhea caused by enterotoxigenic *E. coli*. The method includes administering to the mammal an effective amount of an algal preparation that includes a microalgae and/or extract made from a microalgae. In some embodiments the microalgae is a *Chlamydomonas* sp. In some embodiments the microalgae is *Chlamydomonas reinhardtii* (*C. reinhardtii*). In some embodiments the algae are wild type algae.

In certain embodiments, the algal preparation is administered from about 1 day to about 90 days. In some embodiments, the administration occurs for about 1, 2, 3, 4, 5, 6, 7, 8, 9, 10, 11, 12, 13, 14, 15, 20, 25, 30, 60 or 90 days. In some embodiments, the algal preparation is administered from 3 days to about 60 days, from 3 days to about 30 days, from 3 days to about 14 days or from 3 days to about 7 days.

In some embodiments, the algal preparation is administered from 4 days to about 60 days, from 4 days to about 30 days, from 4 days to about 14 days or from 4 days to about 7 days. In particular embodiments, the algal preparation is administered to the mammal through the alimentary canal. In some embodiments, the algal preparation is administered orally. In some embodiments, the amount of algae administered is between about 0.2% and about 1.0% of total dietary intake on a dry weight basis. In some embodiments, the amount of algae administered is between 6 mg/kg of body weight and 30 mg/kg of body weight.

In some embodiments, the algal preparation is prepared from the whole cells of the microalgae. In some embodiments, the algal preparation is incorporated into a meal, ration, feed, foodstuff or a food product that is administered to the mammal. In other embodiments, the algal preparation is mixed with a liquid for administration to the mammal. In other embodiments, the algal preparation is administered as a dry powder, which may or may not be encapsulated such as in a capsule, tablet, or pill. In still other embodiments, the algal preparation is administered as a slurry. Thus, the embodiments provide for the use of such algal preparations for the treatment of GI tract diseases and conditions in the mammal.

In some embodiments, the mammal is a human. In some embodiments, the mammal is a domestic animal such as a domestic livestock species. In still other embodiments, the mammal is a companion animal such as a dog, cat, rabbit, hamster, gerbil, guinea pig, rat, mouse or the like. In other embodiments the mammal is a laboratory animal such as rodent (such as a rat, mouse hamster or gerbil), a rabbit, a monkey or a pig.

Provided herein are methods treating GI tract diseases and conditions in a mammal in need thereof to result in a decrease or alleviation of the incidence of at least one of the symptoms of the disease or condition. Such symptoms include diarrhea, abdominal pain, weight loss and combinations thereof. In some embodiments, the methods result in a reduction or alleviation of the incidence and/or severity of diarrhea. In some embodiments, the methods result in a reduction or alleviation of the rate of weight loss. In some embodiments, the methods result in a weight stabilization or weight gain. Thus, the embodiments provide for the use of such algal preparations for the treatment of and/or reduction of at least one of the symptoms associated with GI tract diseases and conditions.

Also provided herein are compositions of a Chlampydomonas microalgae formulated for administration to a mammal in an effective amount to reduce or alleviate one or more symptoms of a GI tract disease or condition. Such symptoms include diarrhea, abdominal pain, weight loss and combinations thereof. In some embodiments, administration of the compositions results in a reduction or alleviation of the incidence and/or severity of diarrhea. In some embodiments, administration of the compositions results in a reduction or alleviation of the rate of weight loss. In some embodiments, administration of the compositions results in a weight stabilization or weight gain in the mammal.

In some embodiments, the composition contains an algal preparation of microalgae, where the microalgae is a *Chlamydomonas* sp. In some embodiments, the *Chlamydomonas* sp. in the composition is *Chlamydomonas reinhardtii*. In some embodiments, the *Chlamydomonas* are wild type algae.

In some embodiments, the *Chlamydomonas* of the composition is formulated as a dry powder. In some embodiments, the *Chlamydomonas* of the composition is formulated as a liquid slurry. In some embodiments, the composition is formulated a foodstuff or nutritional supplement. In some embodiments, the *Chlamydomonas* of the composition is formulated to provide from about 0.2% to about 1.0% of dietary intake on a dry weight basis. In some embodiments, the *Chlamydomonas* of the composition is formulated to provide an effective dose range of the microalgae from about 1 mg/kg of body weight to about 40 mg/kg of body weight. In some embodiments, the *Chlamydomonas* of the composition is formulated to provide effective dose ranges from about 6 mg/kg of body weight to about 30 mg/kg of body weight.

In some embodiments, the *Chlamydomonas* of the composition is formulated to provide nutritional supplementation to the mammal. Such supplementation can provide a protein content from about 40%, 42%, 44%, 46%, 48% or 50% total content by weight. In some embodiments, the nutritional supplementation provides omega oils including omega 3, omega 6, omega 9 and a combination thereof. In some embodiments, the nutritional supplementation provides vitamin A. In some embodiments, the nutritional supplementation provides a mineral such as iron, calcium or a combination thereof.

In some embodiments, the composition is formulated as a capsule. In some embodiments, the composition is formulated as a tablet. In some embodiments, the composition is provided as a dietary regime. In some embodiments, the composition is provided in a kit. The kit may include one or more doses of the composition in one or more containers. The doses may be provided as a single multidose aliquot or separated into individual doses. In some embodiments, the kit includes doses sufficient for administration for a period from about 1 day, about 3 days, about 4 days, about 7 days, about 10 days, about 14 days, about 30 days, about 60 days, or about 90 days.

Also provided herein are methods of growing and preparing *Chlamydomonas* biomass for administration to a mammal in need of treatment for a gastrointestinal condition or disease by growing a *Chlamydomonas* sp. under heterotrophic conditions, and harvesting the *Chlamydomonas* biomass. In some embodiments, the *Chlamydomonas* sp. is a *Chlamydomonas reinhardtii*. In some embodiments, the step of growing is performed in the absence of light.

BRIEF DESCRIPTION OF THE DRAWINGS

These and other features, aspects, and advantages of the present disclosure will become better understood with regard to the following description, appended claims and accompanying figures where:

DETAILED DESCRIPTION

The following detailed description is provided to aid those skilled in the art in practicing the claimed invention. This detailed description should not, however, be construed to unduly limit the claimed invention as modifications and variations in the embodiments discussed herein can be made by those of ordinary skill in the art without departing from the scope of the presently claimed inventive discovery.

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

As used in this specification and the appended claims, the singular forms "a", "an" and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges can independently be included or excluded in the range, and each range where either, neither or both limits are included in the smaller ranges is also encompassed, subject to any specifically excluded limit in the stated range. Where the stated range includes one or both of the limits, ranges excluding either or both of those included limits are also included.

Provided herein are methods for the treatment of GI tract diseases and conditions and for treatment, reduction and alleviation of one or more symptoms of a GI tract disease or condition with a microalgae *Chlamydomonas* sp. In one embodiment, the *Chlamydomonas* is a wild-type microalgae. By wild-type microalgae is meant an algae whose genetic make-up has not been altered by the used of recombinant DNA technology. Wild-type algae can be naturally occurring algae found in nature. As used herein, wild type algae can also include algae whose genetic make-up has been altered from that found in nature by the application of mating and directed selection.

Algae, as used herein, refer to non-vascular algae and may include organisms classified as microalgae. It should be noted that in the present disclosure the terms microalgae and algae are used interchangeably. Non-limiting examples of genera of microalgae that may be used to practice the methods and/or prepare the compositions disclosed herein include *Prochlorophyta, Rhodophyta, Chlorophyta, Heterokontophyta, Tribophyta, Glaucophyta, Chlorarachniophytes, Euglenophyta, Euglenoids, Haptophyta, Chrysophyta, Cryptophyta, Cryptomonads, Dinophyta, Dinoflagellata, Pyrmnesiophyta, Bacillariophyta, Xanthophyta, Eustigmatophyta, Raphidophyta* and *Phaeophyta*. In one embodiment the algae used herein is of the genus *Chlamydomonas*. In one particular embodiment, the algae used are *Chlamydomonas reinhardtii* (*C. reinhardtii*). In some embodiments, the algae are created by modifying an existing *Chlamydomonas*, through mating, breeding, cross, or protoplast fusion with another strain of algae. In one embodiment, an existing *Chlamydomonas* species is modified through mating, breeding, cross, or protoplast fusion with another *Chlamydomonas* species.

In some embodiments, the *Chlamydomonas* species are *Chlamydomonas* that do not produce or have significantly reduced production of phosphatidyl choline (PC). In some embodiments, the *Chlamydomonas* species selected are *Chlamydomonas* species that do not include *Chlamydomonas debaryana, Chlamydomonas applanate, Chlamydomonas asymmetrica* and *Chlamydomonas sphaeroides*. In some embodiments, the *Chlamydomonas* species selected are *Chlamydomonas* species that do not include *Chlamydomonas debaryana* NIES-2212, *Chlamydomonas applanate* NIES-2202, *Chlamydomonas asymmetrica* NIES-2207 and *Chlamydomonas sphaeroides* NIES-2242. In some embodiments, the *Chlamydomonas* species selected have a lipid content that is less than 25%, 20%, 15%, 10%, 9%, 8% and/or 7% w/w.

The microalgae useful for practicing the methods and/or preparing the compositions disclosed herein can be grown on land, for example, in ponds, aqueducts, or in closed or partially closed bioreactor systems. The algae can also be grown directly in water, for example, in an ocean, sea, lake, river, reservoir, etc. Thus, the algae may be grown in culture systems of different volumes. In one embodiment, the algae, such as *Chlamydomonas*, can be grown, for example, in small scale laboratory systems. Small scale laboratory systems refer to cultures in volumes of less than about 6 liters. In various embodiments, the small scale laboratory culture may be 1 liter, 2 liters, 3 liters, 4 liters, or 5 liters. In another embodiment, the small scale laboratory culture may be less than one liter. In yet another embodiment, the small scale laboratory culture may be 100 milliliters or less. In one embodiment the culture may be 10 milliliters or less. In another embodiment the culture may be 5 milliliters or less. In yet another embodiment, the culture may be 1 milliliter or less.

Alternatively, the culture systems may be large scale cultures such as large scale cultures of *Chlamydomonas*, where large scale cultures refers to growth of cultures in volumes of greater than about 6 liters, or greater than about 10 liters, or greater than about 20 liters. Large scale cultures can also refer to growth of cultures in volumes of 50 liters or more, 100 liters or more, or 200 liters or more. Thus, large scale cultures can be growth of cultures in, for example, ponds, containers, vessels, or other areas, where the pond, container, vessel, or area that contains the culture is for example, at least 5 square meters, at least 10 square meters, at least 200 square meters, at least 500 square meters, at least 1,500 square meters, at least 2,500 square meters, in area, or greater.

The present disclosure further provides for production of algae, including *Chlamydomonas*, in very large scale culture systems. A very large scale liquid culture system may be from 10,000 to 20,000 liters. In various embodiments, the very large scale culture system may be from 10,000 to 40,000 liters or from 10,000 to 80,000 liters. In various embodiments, the very large scale culture system may be from 10,000 to 100,000 liters or from 10,000 to 150,000 liters. In yet other embodiments, the culture system may be from 10,000 to 200,000 liters or from 10,000 to 250,000 liters. The present disclosure also includes culture systems from 10,000 to 500,000 liters or from 10,000 to 600,000 liters. The present disclosure further provides for culture systems from 10,000 to 1,000,000 liters.

In an aspect of the present disclosure, the culture system may be a pond, either natural or artificial. In one embodiment, the artificial pond may be a raceway pond. In a raceway pond, the algae, water, and nutrients circulate around a "racetrack." Means of motivation, such as paddlewheels, provide constant motion to the liquid in the racetrack, allowing for the organism to be circulated back to the surface of the liquid at a chosen frequency. Paddlewheels also provide a source of agitation to oxygenate the system. $CO_2$ may be added to a culture system as a feedstock for photosynthesis through a $CO_2$ injection system. These raceway ponds can be enclosed, for example, in a building or a greenhouse, or can be located outdoors. In an embodiment, an outdoor raceway culture system may be enclosed with a cover or exposed to the environment.

Alternatively, microalgae such as *Chlamydomonas* can be grown in closed structures such as bioreactors, where the environment is under stricter control than in open systems or semi-closed systems. A photobioreactor is a bioreactor which incorporates some type of light source to provide photonic energy input into the reactor. The term bioreactor can refer to a system closed to the environment and having no direct exchange of gases and/or contaminants with the environment. A bioreactor can be described as an enclosed, and in the case of a photobioreactor illuminated, culture vessel designed for controlled biomass production of liquid cell suspension cultures. Examples of bioreactors include, but are not limited to, glass containers, stainless steel containers, plastic tubes, tanks, plastic sleeves, and bags. In the case of photobioreactors, examples of light sources that can be used include, but are not limited to, fluorescent bulbs, LEDs, and natural sunlight. Because these systems are closed everything that the organism needs to grow (for example, carbon dioxide, nutrients, water, and light) must be introduced into the bioreactor.

Despite their costs to set up and maintain, bioreactors have several advantages over open systems. They can, for example, prevent or minimize contamination, permit axenic organism cultivation of monocultures (i.e., a culture consisting of only one species of organism), offer better control over the culture conditions (for example, pH, light, carbon dioxide, and temperature), prevent water evaporation, lower carbon dioxide losses due to out gassing, and permit higher cell concentrations. On the other hand, certain requirements of bioreactors, such as cooling, mixing, control of oxygen accumulation and biofouling, make these systems more expensive to build and operate than open systems or semi-closed systems.

Microalgae, including *Chlamydomonas*, can be continually harvested (as is with the majority of the larger volume cultivation systems), or harvested one batch at a time (for example, as with polyethylene bag cultivation). Batch harvesting is set up with, for example, nutrients, an organism (for example, microalgae), and water, and the organism is allowed to grow until the batch is harvested. With continuous harvesting, a portion of the algal mass can be harvested, for example, either continually, daily, or at fixed time intervals.

Algae, such as *Chlamydomonas*, may be grown under conditions which permit photosynthesis, however, this is not a requirement (e.g., the organism may be grown in the absence of light). *Chlamydomonas* used in the practice of the present disclosure may be phototrophic, mixotrophic or heterotrophic. Phototrophic or photoautotrophic algae are algae that use photon capture as a source of energy and can fix inorganic carbon. As such, phototrophic algae are capable of using inorganic carbon in the presence of light as a source of metabolic carbon. As used herein, heterotrophic algae refers to algae than cannot use photon capture as an energy source, but must instead rely on organic carbon sources. Mixotrophic algae are those algae that are capable of using photon capture and inorganic carbon fixation to support growth, but in the absence of light may use organic carbon as an energy source. Thus, mixotrophic algae have the metabolic characteristics of both phototrophic and heterotrophic algae.

In growth conditions where a microorganism is not capable of photosynthesis (naturally or due to selection), the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/or any organism-specific requirement. Organic carbon sources include any source of carbon which the host organism is able to metabolize including, but not limited to, acetate, simple carbohydrates (e.g., glucose, sucrose, lactose), complex carbohydrates (e.g., starch, glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

In some embodiments, *Chlamydomonas* are grown heterotrophically. In certain embodiments, *Chlamydomonas* are grown in the absence of light. Methods for the production of high density algae cultures in the absence of light, including *Chlamydomonas*, can be found in, for example, Int'l. Pub. No. WO 2018/038960, entitled IMPROVED METHOD FOR GROWING ALGAE, which is incorporated herein by reference in its entirety. In some embodiments, *Chlamydomonas* are grown heterotrophically and without light.

In certain instances, it may be desirable to reduce the amount of liquid contained in the culture of microalgae, such as *Chlamydomonas*, prior to administration to a patient or incorporation into a food or feedstuff. Separation of the *Chlamydomonas* biomass from the liquid may be accomplished by methods known to one of ordinary skill in the art. In one aspect, the microalgae may be allowed to settle by gravity and the overlying liquid removed. In another aspect, the *Chlamydomonas* biomass may be harvested by centrifugation of the microalgae containing culture. In an aspect, centrifugation of the liquid culture may be performed in batch mode, using a fixed volume centrifuge. In a different aspect, batch harvesting of the *Chlamydomonas* may be accomplished using a continuous flow centrifuge. In another aspect, the *Chlamydomonas* may be harvested continuously from the growing culture by continuous flow centrifugation. In other aspects, liquid removal may be accomplished by filtration, for example, tangential flow filtration. In other aspects, reduction in the liquid content may be accomplished by electrophoresis techniques such as electrolytic coagulation and electrolytic flocculation.

In some embodiments, an even a greater reduction in the liquid content of the *Chlamydomonas* preparation may be required or desirable. Thus, in some embodiments, the moisture content of the algae preparation may be less than 15% moisture, less than 10% moisture, less than 9% moisture, less than 8% moisture, less than 7% moisture, less than 6% moisture, less than 5% moisture, less than 4% moisture or less than 3% moisture. Reduction of moisture content to below 15% moisture can be achieved by any method known in the art, and is typically achieved by the use of a drying apparatus. Dryers that may be used in the practice of the currently disclosed methods include, but are not limited to, rotary vacuum dryers, rotary tunnel dryers, fluid bed dryers, pneumatic dryers, plate dryers, tray dryers, drum dryers, spray dryers, flash dryers, freeze dryers, pan dryers, paddle dryers, microwave dryers and solar drying.

In a rotary drum dryer, a horizontal, cylindrical, jacketed shell surrounds an agitator rotating in close tolerance. Drying is accomplished under vacuum, with heat supplied through the jacket. In a rotary tunnel dryer, the material is travels through an inclined, horizontal rotating cylinder and moisture is removed through heated air flowing through the cylinder. In fluid bed dryers, the material is suspended against gravity by means of an upward flowing air stream. There may also be a horizontal air flow to move the material through the dryer. In a pneumatic dryer, the moisture is removed by conveying the material in rapidly moving heated air. The velocity and turbulence of the air stream maintains the material in suspension and facilitates liquid removal. A flash dryer, is a version of a pneumatic dryer in which the material has a short residence time in the drying unit, thus flashing off the moisture. In a drum or roller dryer, the material is spread over the surface of a heated rotating drum or roller. The material remains on the surface of the drum for the greater part of rotation, during which drying occurs. The dried material is then scrapped off the drum. In a spray dryer, the material is sprayed in fine droplets into a stream of heated air. The air and droplets move in counter current or parallel fashion. The dryer body is large enough to allow the resulting particles to settle as they dry without contacting and sticking to the dryer walls. In a tray dryer, the a thin layer of the material is spread out on a tray in which drying takes place. Heating of the material to be dried is accomplished by heated air moving across the trays, conduction from heated trays or shelves holding the trays, radiation from heated surfaces, or a combination of these. In a paddle dryer, the material is agitated by heated rotating blades or paddles so that new material is continuously exposed to the heated surface to evaporate the liquid. In a plate dryer, the material is transferred over a series of stacked horizontal heated plates. Microwave dryers, use microwaves to excite water molecules to cause them to vaporize. In freeze drying, the material is frozen, usually to about −70° C. to −100° C. and exposed to a vacuum so that the moisture is removed by sublimation. In solar drying the material is place in a thin layer exposed to the sun and the water allowed to evaporate. Additional means of drying will be readily apparent to those of skill in the art.

The exact conditions for drying the algae preparation will depend on the type of dryer used. In general, conditions are selected to minimize the amount of heat damage to the algal material during the drying process. More specifically, conditions are generally selected to minimize the denaturation of algal proteins during the drying process. It is well within the abilities of one skilled in the art to select methods and conditions in order to minimize heat damage during the drying process.

In some instances the *Chlamydomonas* preparation will be washed after harvesting and prior to administration to a subject or prior to processing into a form for administration to a subject. Any method known in the art may be used to wash the *Chlamydomonas* to remove, for example, salts or other components of the culture medium. In one embodiment, the *Chlamydomonas* is partially dewatered, for example by centrifugation as described herein, and then resuspended in a desired liquid, such as potable water or other liquid for ingestion. This washing process may be carried out more than once, for example, twice, three times, or four times.

The *Chlamydomonas* compositions described herein may be administered to a mammal/subject in need of treatment. A mammal in need of treatment is considered an animal, including a human, suffering from the symptoms of, or diagnosed with, a GI tract disease or condition. In some embodiments, the mammal is a human, while in other embodiments the mammal is a non-human. In certain embodiments the mammal is a companion animal. A companion animal is an animal that is kept as a "pet" by a person for companionship and enjoyment. Non-limiting examples of companion animals include cats, dogs, ferrets, rabbits, hamsters, guinea pigs, rats, and gerbils. In some cases, companion animals can include large domestic species such as horses, goats, llamas, vicunas, alpacas, pigs and donkeys. In some embodiments, the mammal is a domestic livestock species. Livestock refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, llamas, vicunas, alpacas, domestic buffalo, elk, deer, and rabbits. In certain embodiment, the mammal is a laboratory animal such as a rodent, a mouse, a rat, a rabbit, a primate, a monkey a piglet or a pig.

The *Chlamydomonas* may be administered as part of a liquid or semi-liquid preparation. By a liquid or semi-liquid preparation is meant a preparation containing at least about 30% and up to about 99% liquid. In some embodiments, the preparation contains from about 40% to about 95% liquid. In other preparations, the liquid content is between about 50% and about 95%. In other embodiments, the algae preparation is 99%, 98%, 97%, 96%, 95%, 94%, 93%, 92%, 91%, 90%, 89%, 88%, 87%, 86%, 85%, 84%, 83%, 82%, 81% or 80% liquid. Liquid preparations will usually be administered orally (i.e., by mouth). The *Chlamydomonas* may be mixed with water or any other liquid suitable for ingestion by the subject to be treated. In the case of a suckling animal, the algae may be incorporated into, or otherwise mixed with, milk or a milk replacement. The liquid *Chlamydomonas* preparation may include additional substances to increase palatability such as natural and artificial sweeteners and flavorings. In some embodiments, the preparation may contain natural or artificial sweeteners such as sugar (cane or beet), high fructose corn syrup, molasses, honey, agave syrup, maple syrup, brown rice syrup, barley malt syrup or crystals, coconut sugar, stevia (stevioside), fructose crystals, aspartame, cyclamate, saccharine, sucralose and neotame. In some embodiments, the algae may be mixed with a fruit or vegetable puree. In other embodiments, the *Chlamydomonas* may be mixed with a dairy product, and in particular a cultured dairy product such as yogurt. One of skill in the art will appreciate that plant based substitutes for dairy products such as soy milk, soy yogurt, almond milk or almond yogurt may also be utilized. Although the various additions have been listed separately, it should be appreciated that they can be mixed in any combination, for example, algae with cane sugar, fruit puree and yogurt to produce a liquid or semi-liquid preparation for ingestion.

In various embodiments, the *Chlamydomonas* may be formulated or ingested in a dry form, for example, a preparation having 15% or less moisture content. As such, the *Chlamydomonas* may be administered to the patient or subject in the form of a capsule, tablet, pill, powder, or granules. In such solid dosage forms, the *Chlamydomonas* may be combined with one or more adjuvants such as lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. In other instances, the *Chlamydomonas* may be compressed into biscuits, wafers or pellets for ingestion. The dried *Chlamydomonas* may also be incorporated into other feeds or foodstuffs to provide additional nutrition to the patient and/or to increase palatability.

In some embodiments, the *Chlamydomonas* preparation may be administered directly into the colon of the patient/subject to be treated. In such embodiments, the algae may be administered into the colon in the form of a suppository by the incorporation of conventional suppository bases, such as cocoa butter or other glycerides, into the composition. In other embodiments, a liquid *Chlamydomonas* preparation may be administered into the colon by way of an enema and, in particular, a retention enema.

In some embodiments, the *Chlamydomonas* preparation may be formulated for nutritional supplementation. Such supplementation can provide an algal protein content from about 40%, 42%, 44%, 46%, 48% or 50% total content by weight. In some embodiments, the nutritional supplementation provides one or more omega oils, including omega 3, omega 6, omega 9 and a combination thereof. In some embodiments, the nutritional supplementation provides vitamin A. In some embodiments, the nutritional supplementation provides supplementation a mineral including iron, calcium or a combination thereof.

In some embodiments, the composition containing *Chlamydomonas* is provided as a dietary regime. In some embodiments, the composition is provided in a kit. The kit may include one or more doses of the composition in one or more containers. The doses may be provided as a single multidose aliquot or separated into individual doses. In some embodiments, the kit provides doses sufficient for administration for a period from about 1 day, about 3 days, about 4 days, about 7 days, about 10 days, about 14 days, about 30 days, about 60 days, or about 90 days.

When fed to animals, such as livestock or companion animals, the *Chlamydomonas* preparation may be incorporated into a total mixed ration. The ration can be in the form of a loose mixture of feed ingredients or may be formed into a shape for convenient handling and feeding such as a pellet, cube or kibble. In some embodiments the algae preparation may be fed alone as a supplement, while in still other embodiments, the algae preparation may be fed as a "top dressing" by applying the algae preparation to the animal's normal feed.

In another aspect, the *Chlamydomonas* preparation is administered to the patient/subject at a dose effective to alleviate the condition being treated, for example, weight loss associated with colitis, irritable bowel syndrome or diarrhea due to enterotoxigenic *E. coli*. As will be appreciated by one of skill in the art, the exact dosage will vary with the animal being treated and the severity of the condition. In general, an effective dose of algae will be about 0.05% to about 1.0% (w/w) of total dietary intake on a dry weight basis. In some embodiments, the dose is about 0.05%, about 0.06%, about 0.07%, about 0.08% about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9% or about 2.0% of total dietary intake on a dry weight basis. In some embodiments, the dose is about 1 mg/kg of body weight, about 2 mg/kg of body weight, about 3 mg/kg of body weight, about 4 mg/kg of body weight, about 5 mg/kg of body weight, about 6 mg/kg of body weight, about 7 mg/kg of body weight, about 8 mg/kg of body weight, about 9 mg/kg of body weight, about 10 mg/kg of body weight, about 11 mg/kg of body weight, about 12 mg/kg of body weight, about 13 mg/kg of body weight, about 14 mg/kg of body weight, about 15 mg/kg of body weight, about 16 mg/kg of body weight, about 17 mg/kg of body weight, about 18 mg/kg of body weight, about 19 mg/kg of body weight, about 20 mg/kg of body weight, about 21 mg/kg of body weight, about 22 mg/kg of body weight, about 23 mg/kg of body weight, about 24 mg/kg of body weight, about 25 mg/kg of body weight, about 26 mg/kg of body weight, about 27 mg/kg of body weight, about 28 mg/kg of body weight, about 29 mg/kg of body weight, about 30 mg/kg of body weight, about 31 mg/kg of body weight, about 32 mg/kg of body weight, about 33 mg/kg of body weight, about 34 mg/kg of body weight, about 35 mg/kg of body weight, about 36 mg/kg of body weight, about 37 mg/kg of body weight, 38 mg/kg of body weight, 39 mg/kg of body weight, or about 40 mg/kg of body weight.

As with the exact dosage, the length of treatment may also vary with the severity of the condition. Adjustment of the time course of administration is within the abilities of the skilled healthcare provider. In general, the *Chlamydomonas* preparation will be administered over a period of from about 1 day to about 90 days. In some embodiments, the *Chlamydomonas* preparation is administered for about 1 day, 2 days, 3 days, 4, days, 5 days, 6 days, 7 days, 10 days, 14 days, 21 days, 30 days, 60 days or 90 days. In some embodiments, the algae preparation is administered between about 4 days to about 60 days, about 4 days to about 30 days, about 4 days to about 14 days, or 4 days to about 7 days. In other embodiments, the algae preparation is administered between about 7 days to about 14 days, about 14 days to about 21 days, about 21 days to about 28 days, about 28 days to about 35 days, about 35 days to about 42 days, about 42 days to about 49 days, about 49 days to about 56 days, about 56 to about 63 days, about 63 days to about 70 days, about 70 days to about 77 days, about 77 days to about 84 days, about 84 days to about 90 days. In still other embodiments, the treatment period is from 4 days up to about 7 days, up to about 14 days, up to about 21 days, up to about 28 days, up to about 35 days, up to about 42 days, up to about 49 days, up to about 56 days, up to about 63 days, up to about 70 days, up to about 77 days, up to about 84 days or up to about 90 days.

EXAMPLES

Example 1. Effect of Algae on Weight Loss in a Mouse Model of Colitis

Figure 1:
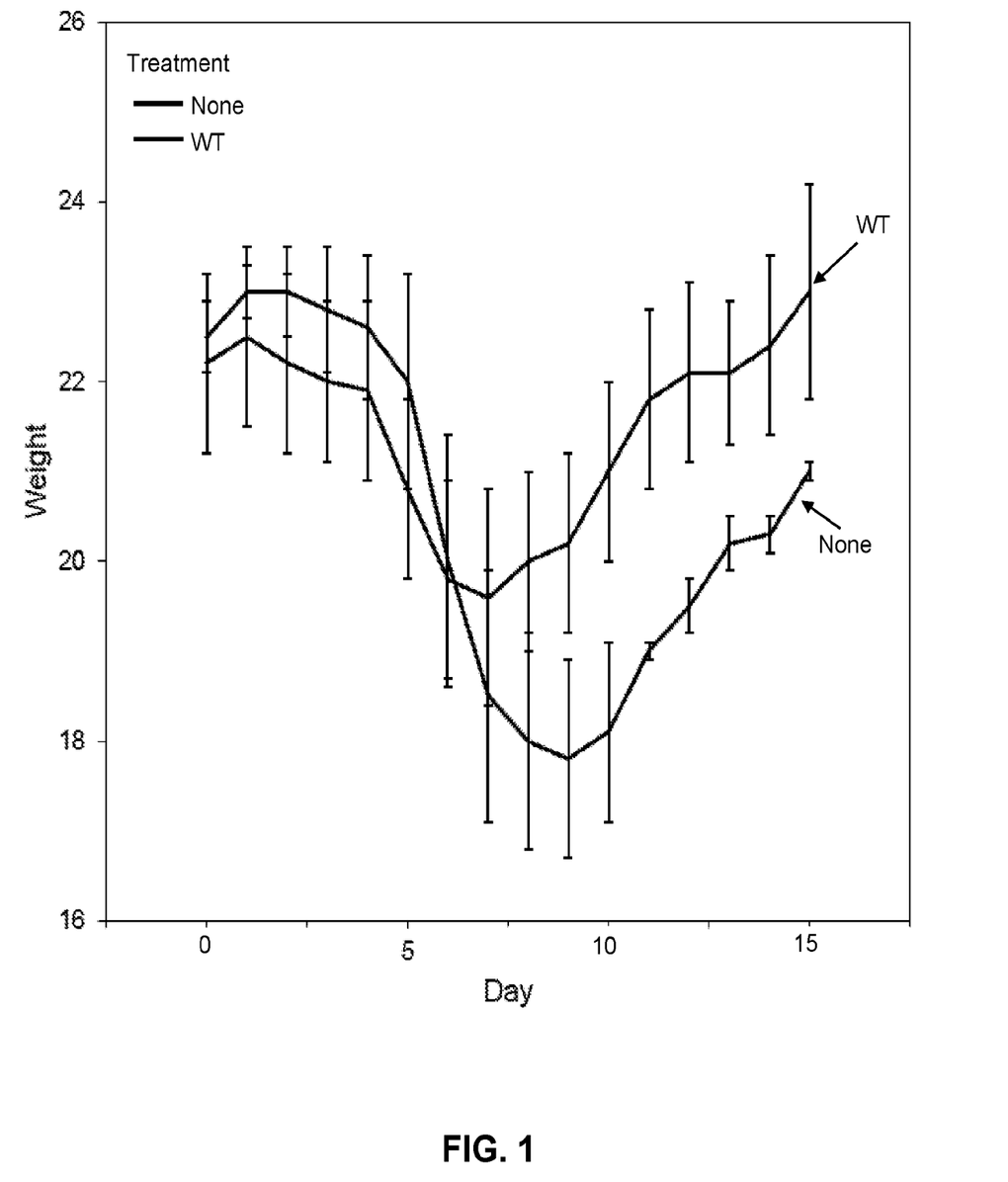
FIG. 1 is a graphical diagram showing that mice fed a diet containing *C. reinhardtii* algae (WT in figure) had a markedly attenuated reduction in weight loss as compared to mice fed a control diet (None in figure) in response to DSS induced colitis.

Twenty-one day old mice were divided into 2 groups of 4 mice each. Group 1 was fed a normal ration of mouse chow for 4 days, while in Group 2, the ration was supplemented with 10 mg/kg of body weight of *Chlamydomonas reinhardtii* algae. The mice were fed their respective diets for 4 days and then administered 3% dextran sodium sulfate (DSS) in their water. Administration of DSS is an established method to induce the symptoms of colitis under experimental conditions. Chassaing B, Aitken J D, Malleshappa M, Vijay-Kumar M: Dextran sulfate sodium (DSS)-induced colitis in mice. *Curr Protoc Immunol* 2014, 104:Unit 15 25. Mice were fed for an additional day after the DSS treatment, and then both groups were fed the normal ration for the remainder of the 15 day trial period. The weight of the mice was monitored daily to determine the effect of feeding algae on weight loss. The results are shown in FIG. 1, which shows the mice receiving the algae had a lower weight loss than mice not treated with the algae.

Example 2. Effect of Algae on Incidence of Diarrhea in New Born Piglets

Figure 2A:
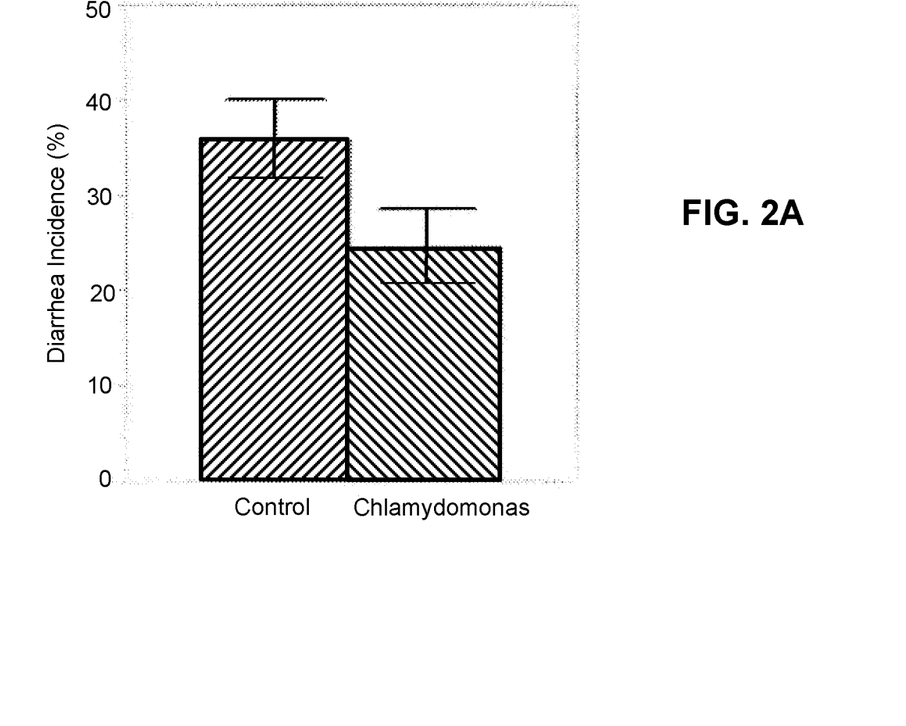
FIGS. 2A and 2B are graphical diagrams showing that piglets fed a diet containing *C. reinhardtii* (*Chlamydomonas* in figures) had a decreased incidence of diarrhea (FIG. 2A) and an increased rate of recovery (FIG. 2B) as compared to controls in response to a challenge with enterotoxigenic *E. coli*.
Figure 2B:
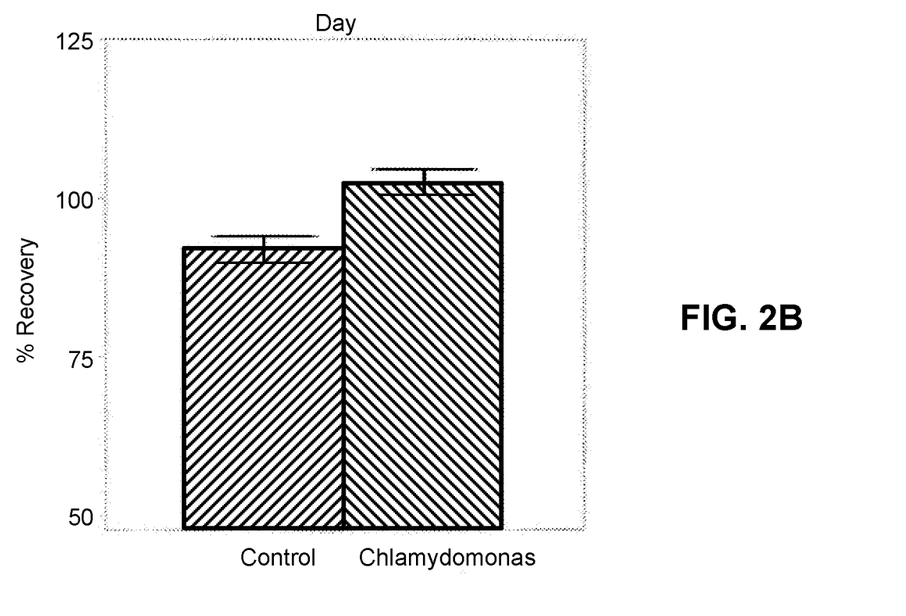
Figure 3:
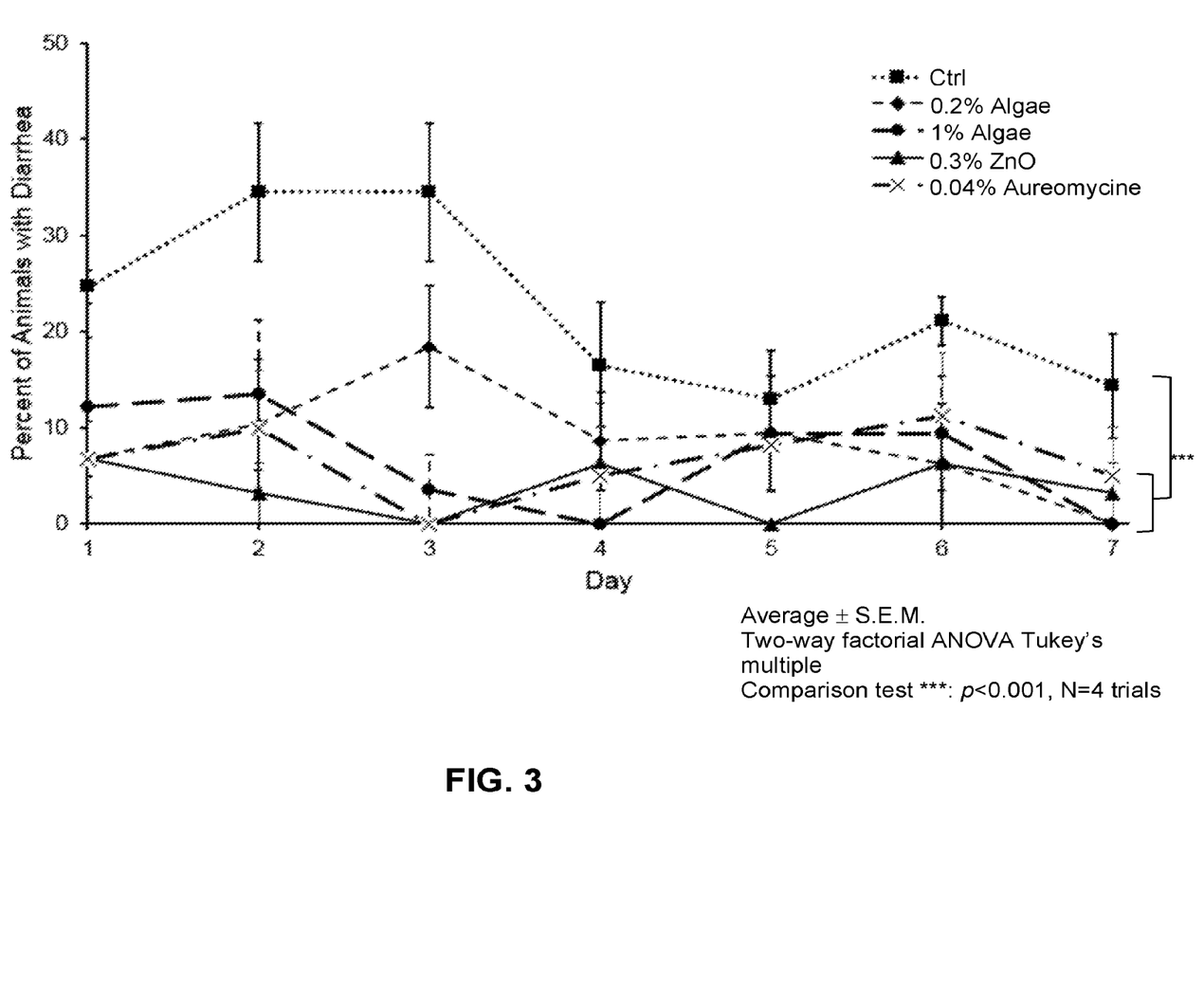
FIG. 3 is a graphical diagram showing a dose dependent, statistically significant reduction in the incidence of diarrhea in piglets fed *C. reinhardtii* algae as compared to controls receiving no treatment. In addition, the figure shows that the incidence of diarrhea was not significantly different in piglets whose diet was supplemented with either zinc oxide or aueromycine as compared to piglets supplemented with algae.

Eight newborn piglets were divided into 2 groups of 4 piglets each. Group 1 served as the control. Piglets in Group 1 were fed standard milk replacer. In Group 2, the standard milk replacer was supplemented with 2.5 grams (dry weight) of *Chlamydomonas reinhardtii* algae per day. Piglets were challenged with a single dose of a hemolytic strain of *E. coli* at 48 hours of birth. The single dose included 3 mL of a solution containing $10^{10}$ CFU of *E. coli*. Piglets were fed and observed 6 times daily until 7 days of age. At each observation, incidences of diarrhea were documented. As can be seen in FIGS. 2A, 2B and 3, administration of algae to newborn pigs reduced the incidence of diarrhea and shortened the recovery time from diarrhea in newborn piglets.

Example 3. Effect of Algae on Incidence of Diarrhea in 21 Day Old Pigs

Twenty-one day old pigs were divided into 5 groups of 24 pigs each. Group 1 served as the control and received no treatment. Group 2 received 0.2% (2 g/kg dry weight of ration) dried *C. reinhardtii* algae in the diet and Group 3 received 1.0% (10 g/kg dry weight of ration) dried *C. reinhardtii* algae in the diet. Groups 4 and 5 received 0.3% (3 g/kg dry weight of ration) of zinc oxide and 0.04% (0.4 g/kg dry weight of diet) of aureomycin. Pigs were raised in outdoor pens to mimic real world conditions and instances of diarrhea were recorded daily.

In light of the detailed description and the examples presented above, it can be appreciated that the several aspects of the invention are achieved.

It is to be understood that the claimed invention has been described in detail by way of illustration and example in order to acquaint others skilled in the art with the claimed invention, its principles, and its practical application. Particular formulations and processes of the claimed invention are not limited to the descriptions of the specific embodiments presented, but rather the descriptions and examples should be viewed in terms of the claims that follow and their equivalents. While some of the examples and descriptions above include some conclusions about the way the claimed invention may function, the inventors do not intend to be bound by those conclusions and functions, but puts them forth only as possible explanations.

It is to be further understood that the specific embodiments set forth above are not intended as being exhaustive or limiting of the claimed invention, and that many alternatives, modifications, and variations will be apparent to those of ordinary skill in the art in light of the foregoing examples and detailed description. Accordingly, the claimed invention is intended to embrace all such alternatives, modifications, and variations that fall within the scope of the following claims.

What is claimed is:

1. A method for treating weight loss in a mammal suffering from or diagnosed with a disease or condition associated with inflammation of the gastrointestinal tract, comprising administering to the mammal an effective amount of *Chlamydomonas reinhardtii*.

2. The method of claim 1, wherein *C. reinhardtii* does not produce phosphatidyl choline.

3. The method of claim 1, wherein *C. reinhardtii* has a lipid content that is less than about 25%, 20%, 15%, 10%, 9%, 8% or 7% w/w.

4. The method of claim 1, wherein *C. reinhardtii* has not been genetically engineered.

5. The method of claim 1, wherein the disease or condition is selected from the group consisting of colitis, irritable bowel syndrome, inflammatory bowel disease, Crohn's disease, ulcerative colitis, and post infection colitis.

6. The method of claim 5, wherein the disease or condition is associated with a symptom of diarrhea, abdominal pain, or a combination thereof.

7. The method of claim 6, wherein the administration results in a decreased incidence of at least one of the symptoms as compared to the incidence of the at least one symptom prior to administration.

8. The method of claim 1, wherein the administration results in a decreased rate of weight loss of the mammal as compared to the rate of weight loss prior to administration.

9. The method of claim 1, wherein the administration results in weight gain as compared with the mammal's starting weight prior to the administration.

10. The method of claim 1, wherein *C. reinhardtii* is administered for at least 3 days.

11. The method of claim 1, wherein the effective amount is from about 0.2% to about 1.0% of dietary intake on a dry weight basis.

12. The method of claim 1, wherein the effective amount is from about 1 mg/kg of body weight to about 40 mg/kg of body weight.

13. The method of claim 1, wherein a total period of administration is selected from about 1 day, about 3 days, about 4 days, about 7 days, about 10 days, about 14 days, about 30 days, about 60 days and about 90 days.

14. The method of claim 1, wherein the administration is alimentary administration.

15. The method of claim 14, wherein the administration is oral administration.

16. The method of claim 14, wherein *C. reinhardtii* is incorporated into a foodstuff or nutritional supplement.

17. The method of claim 1, wherein the mammal is a human, a domestic animal, a livestock, a pet or a companion animal.

18. The method of claim 17, wherein the mammal suffers from diarrhea caused by enterotoxigenic *E. coli*, and wherein the administration of *C. reinhardtii* is effective to decrease the incidence or duration of the diarrhea in the mammal.

19. The method of claim 1, wherein *C. reinhardtii* has been growth heterotrophically.

* * * * *

UNITED STATES PATENT AND TRADEMARK OFFICE
CERTIFICATE OF CORRECTION

PATENT NO. : 11,311,584 B2
APPLICATION NO. : 16/609398
DATED : April 26, 2022
INVENTOR(S) : Miller Tran et al.

It is certified that error appears in the above-identified patent and that said Letters Patent is hereby corrected as shown below:

In the Specification

In Column 1, Line 20, "(BID)" should read as -- (IBD) --

Signed and Sealed this
Twenty-fourth Day of May, 2022

Katherine Kelly Vidal
*Director of the United States Patent and Trademark Office*